(12) United States Patent
Nagai et al.

(10) Patent No.: US 6,909,269 B2
(45) Date of Patent: Jun. 21, 2005

(54) PARTICLE DETECTOR AND PARTICLE ANALYZER EMPLOYING THE SAME

(75) Inventors: Takaaki Nagai, Kobe (JP); Koichi Okubo, Kobe (JP); Kunio Ueno, Kakogawa (JP)

(73) Assignee: Sysmex Corporation, Kobe (JP)

( * ) Notice: Subject to any disclaimer, the term of this patent is extended or adjusted under 35 U.S.C. 154(b) by 26 days.

(21) Appl. No.: 10/305,146

(22) Filed: Nov. 27, 2002

(65) Prior Publication Data

US 2003/0102220 A1 Jun. 5, 2003

(30) Foreign Application Priority Data

| Nov. 30, 2001 | (JP) | 2001-366885 |
| Dec. 5, 2001 | (JP) | 2001-371503 |
| Dec. 5, 2001 | (JP) | 2001-371513 |
| Dec. 5, 2001 | (JP) | 2001-371524 |

(51) Int. Cl.[7] .............................................. G01N 27/00
(52) U.S. Cl. .................................. 324/71.4; 324/71.1
(58) Field of Search .............................. 324/71.1, 71.4, 324/439, 450

(56) References Cited

U.S. PATENT DOCUMENTS

| 3,340,471 A | 9/1967 | Coulter, Jr. ............... 324/71.1 |
| 3,515,884 A | 6/1970 | Imadate ........................ 377/12 |
| 3,688,191 A | 8/1972 | Claps ......................... 324/71.1 |
| 3,710,933 A | 1/1973 | Fulwyler et al. ............. 209/3.1 |
| 3,783,376 A | 1/1974 | Doniguian ................. 324/71.1 |
| 3,958,177 A | 5/1976 | Reeves et al. ............. 324/71.1 |
| 4,070,617 A | 1/1978 | Kachel et al. ............. 324/71.1 |
| 4,375,615 A | 3/1983 | Haynes ...................... 324/71.4 |
| 4,564,803 A | 1/1986 | Loren et al. ............... 324/71.1 |
| 4,891,575 A | 1/1990 | Kogo et al. ............... 324/71.1 |
| 5,905,214 A | 5/1999 | Inami ....................... 73/865.5 |
| 6,417,658 B1 | 7/2002 | Inami ....................... 324/71.4 |

FOREIGN PATENT DOCUMENTS

| EP | 0398719 A | 11/1990 |
| EP | 0844475 A | 5/1999 |
| EP | 1069423 A2 | 1/2001 |
| GB | 1348881 A | 3/1974 |
| JP | 58-129349 A | 8/1983 |
| JP | 8-15125 A | 1/1996 |
| JP | 11-87981 A | 3/1999 |
| JP | 2001-33378 A | 2/2001 |

Primary Examiner—Vincent Q. Nguyen
(74) Attorney, Agent, or Firm—Birch, Stewart, Kolasch & Birch, LLP

(57) ABSTRACT

A particle detector includes first and second cells, the first cell supplying a liquid containing particles to the second cell; electrodes respectively provided in the first cell and the second cell; a plurality of shafts; and clamp members engaged with the respective shafts; the first cell and the second cell being arranged in alignment with each other; the shafts extending through the first cell and the second cell along the alignment of the first cell and the second cell; the clamp members clamping the first cell and the second cell along the alignment.

22 Claims, 12 Drawing Sheets

PARTICLE DETECTOR AND PARTICLE ANALYZER EMPLOYING THE SAME

CROSS-REFERENCE TO RELATED APPLICATION

This application is related to Japanese Patent Applications No. 2001-366885 (filed on Nov. 30, 2001), No. 2001-371503 (filed on Dec. 5, 2001), No. 2001-371513 (filed on Dec. 5, 2001) and No. 2001-371524 (filed on Dec. 5, 2001), whose priorities are claimed under 35 USC §119, the disclosures of which are incorporated by reference in their entirety.

BACKGROUND OF THE INVENTION

1. Field of the Invention

The present invention relates to a particle detector and, more particularly, to a particle detector employing an electrical detection zone method for measuring the number and size of particles such as of fine ceramic powder, a pigment or cosmetic powder, wherein the number and size of particles contained in a particle containing liquid are measured on the basis of a change in electric impedance detected when the particle containing liquid is caused to pass through a through-hole.

2. Description of the Related Art

A particle detector known in relation to the present invention comprises: a detection block having a through-hole for particle detection; a first cell which supplies a particle containing liquid enclosed in a sheath liquid into the through-hole; a second cell which receives and discharges the particle containing liquid and the sheath liquid having passed through the through-hole; electrodes respectively provided in the first and second cells; and a slidable member slidably supporting one of the first and second cells so that a distance between the first and second cells can be changed; wherein the detection block is removably held between the first and second cells to liquid-tightly connect the first and second cells to each other (see, for example, Japanese Unexamined Patent Publication No. 2001-33378).

Further, there is known a noise-shielding rack for electronic devices, which has a double structure including an inner body, an outer body and an insulative member interposed therebetween, wherein the inner body directly houses an electronic device and the outer body is grounded (see, for example, Japanese Unexamined Patent Publication No. HEI11(1999)-87981).

Conventionally, an electrical detection zone method is employed for measuring the number and size of blood cells in blood, or particles such as cement powder, latex or toner for industrial use. In the electrical detection zone method, a partition having a single through-hole is provided in an electrolytic solution, and two electrodes are disposed on opposite sides of the through-hole. Particles to be subjected to the measurement are dispersed in the electrolytic solution, and the resulting particle containing liquid is caused to flow through the through-hole.

When the particles pass through the through-hole, an electrical resistance is instantaneously changed, and voltage pulses are generated between the electrodes. The height $\Delta V$ of each of the pulses reflects on the volume $V_p$ of a particle as expressed by the following expression:

$$\Delta V = I \cdot \rho \cdot V_p / S^2 \qquad (1)$$

(wherein I is a constant electric current flowing between the electrodes, S is a sectional area of the through-hole, and $\rho$ is the electrical resistance of the electrolytic solution). Therefore, the sphere equivalent diameter of the particle can be determined irrespective of the shape of the particle. As a result, the volume-based size of the particle can be determined. Further, the number of the particles can be determined on the basis of the number of the pulses.

However, the conventional particle detector has the following drawbacks.

(1) The electrical detection zone method suffers from problems such that the intensity of a detection signal varies depending on the position of the particle within the through-hole through which the particle passes, that plural particles passing close to each other are counted as one, and that particles having passed through the through-hole stagnate around the through-hole to cause noises. A conventional approach to these problems is to employ a sheath flow method in combination with the electrical detection zone method. In the combination sheath flow method, a stream of a particle containing liquid is enclosed in another liquid (sheath liquid) in a flow cell so as to be narrowed, whereby the particles can be introduced in line into the through-hole along the center axis of the through-hole. Thus, the particle size can be determined with minimum errors. However, it is essential to accurately align the axis of the narrowed stream of the particle containing liquid with the center axis of the through-hole for highly accurate detection in a particle detector based on such a principle. Therefore, how to simplify the construction of the particle detector for the accurate alignment is a problem.

(2) In the particle detector employing the electrical detection zone method, i.e., in the particle detector of electrical resistance type, air bubbles are liable to occur in and around the through-hole when the particle containing liquid flows through the through-hole. If the amount of the air bubbles increases, detection pulses between the electrodes are disturbed, so that information on the particles is erroneously detected.

(3) During repeated particle detection, minute substances such as particle pieces are deposited in the through-hole, so that a sectional area S of the through-hole is varied. With the variation in the sectional area S, pulse heights $\Delta V$ detected for particles having the same volume $V_p$ differ as can be understood from the expression (1). Therefore, it is difficult to continuously provide detection results with acceptable reproducibility.

(4) In the particle detector of electrical resistance type, noises in the voltage pulses obtained when the particles pass through the through-hole are liable to be enhanced under an influence of external electromagnetic noises. This may reduce the detection accuracy. In recent years, therefore, the European Union (EU) has required medical electronic measuring apparatuses to conform with standards specified by the EMC regulations, i.e., to ensure that measurements are not influenced by radio waves having a specified field intensity.

SUMMARY OF THE INVENTION

In accordance with the present invention, there is provided a particle detector, which comprises: first and second cells, the first cell supplying a liquid containing particles to the second cell; electrodes respectively provided in the first cell and the second cell; a plurality of shafts; and clamp members engaged with the respective shafts; the first cell and the second cell being arranged in alignment with each other; the shafts extending through the first cell and the second cell along the alignment of the first cell and the second cell; the clamp members clamping the first cell and the second cell along the alignment.

DESCRIPTION OF THE PREFERRED EMBODIMENTS

Figure 1:
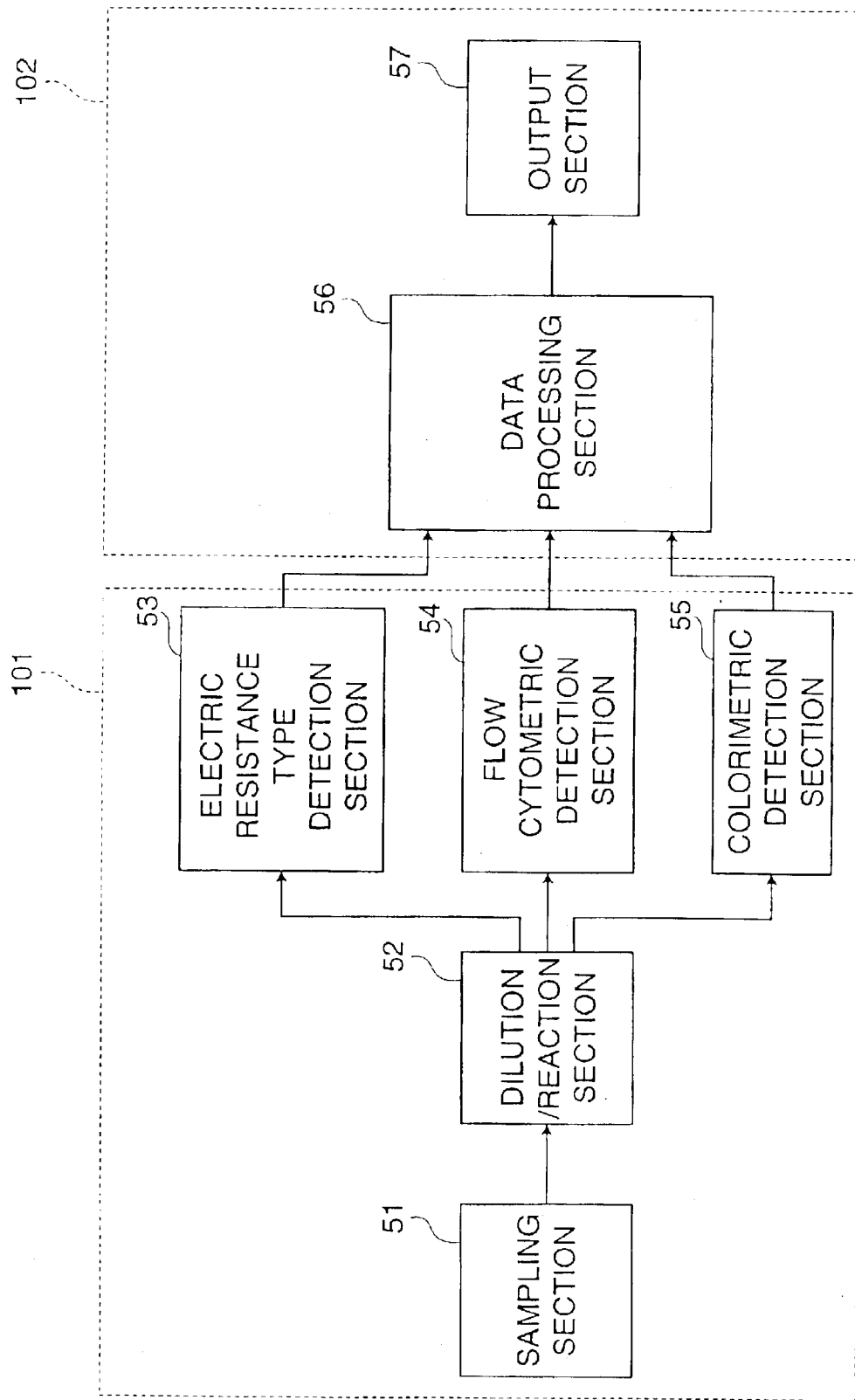
FIG. 1 is a block diagram illustrating the construction of a particle analyzer according to the present invention.

In accordance with one inventive aspect, there is provided a particle detector, which comprises: first and second cells, the first cell supplying a liquid containing particles to the second cell; electrodes respectively provided in the first cell and the second cell; a plurality of shafts; and clamp members engaged with the respective shafts; the first cell and the second cell being arranged in alignment with each other; the shafts extending through the first cell and the second cell along the alignment of the first cell and the second cell; the clamp members clamping the first cell and the second cell along the alignment. According to this inventive aspect, the shafts extend through the first and second cells of the particle detector for positioning the first and second cells, so that the particle detector can easily and accurately be assembled with a high level of reproducibility.

In the particle detector, a plate member formed with a through-hole may be interposed between the first cell and the second cell. The plate member may comprise a flat piece formed with the through-hole. Alternatively, the first cell may comprise the flat piece formed with the through-hole. Alternatively, the second cell may comprise the flat piece formed with the through-hole. A disk piece, a flat oval piece or a flat polygonal piece may be used as the flat piece.

The flat piece formed with the through-hole may be interposed between the first cell and the second cell.

The first cell may comprise a nozzle which discharges the liquid, and the second cell may comprise a collection tube which collects the liquid discharged from the nozzle, wherein the first cell and the second cell are connected to each other so that the nozzle, the through-hole and the collection tube are arranged coaxially with each other.

The first cell may comprise a nipple which receives a sheath liquid to be supplied to the second cell, and the second cell may comprise a collection tube which collects the supplied sheath liquid.

The first cell may comprise a nozzle support having a nozzle which discharges the liquid containing particles, and a first cell body having a nipple which receives a sheath liquid to the first cell.

The nozzle support and the first cell body may liquid-tightly be connected to each other via a packing.

The second cell may comprise a collection tube support having a collection tube which collects the liquid supplied from the first cell, and a second cell body having a nipple which receives a cleaning liquid to the second cell.

The collection tube support and the second cell body may liquid-tightly be connected to each other via a packing.

In accordance with another inventive aspect, there is provided a particle analyzer employing the aforesaid particle detector.

In accordance with further another inventive aspect, there is provided a particle detector, which comprises: first and second cells, the first cell supplying a liquid containing particles to the second cell; a flat piece formed with a through-hole; and electrodes respectively provided in the first cell and the second cell; the first cell and the second cell communicating with each other through the through-hole, at least one of the first cell and the second cell comprising a first nipple which receives a cleaning liquid to be sprayed toward the through-hole, and a second nipple which drains the sprayed cleaning liquid. According to this inventive aspect, the cleaning liquid is sprayed in and around the through-hole from the first nipple and, together with air bubbles, discharged from the second nipple. Therefore, the particle detection can be performed in a bubble-free state thereby to provide highly accurate detection results.

The first cell and the second cell may each comprise the first nipple and the second nipple.

The first nipple may be disposed so that the cleaning liquid is sprayed at an incident angle of 30 to 60 degrees with respect to an axis of the through-hole.

In accordance with still another inventive aspect, there is provided a particle detector, which comprises: a cylindrical first cell body having openings of its both end; a cylindrical second cell body having openings of its both end; a first cap member having a nozzle which discharges a liquid containing particles; a second cap member having a collection tube which collects the liquid having discharged from the nozzle; electrodes respectively provided in the first cell body and the second cell body; and a plurality of shafts extending through the first cap member, the first cell body, the second cell body and the second cap member; wherein one opening of the first cell body communicates with one opening of the second cell body through a through-hole, the first cap member liquid-tightly closes the other opening of the first cell body in a removable manner, the second cap member liquid-tightly closes the other opening of the second cell body in a removable manner, the nozzle and the collection tube are arranged coaxially with each other, and the first cap member and the second cap member are removable from the plurality of the shafts. According to this inventive aspect, the first and second cap members can be removed from the first and second cell bodies, so that the through-hole and its peripheral area can easily be cleaned by inserting a brush to the opening of the first or second cell body.

The particle detector may further comprise clamp members provided on opposite ends of the respective shafts for clamping the first cell body and the second cell body, wherein the first cap member and the second cap member are disengageably engaged with the clamp members to close the first cell body and the second cell body, respectively.

At least one of the electrodes may be incorporated in the first cap member or the second cap member.

The first cap member and the second cap member may respectively have holes through which the clamp members are respectively inserted, wherein the holes are configured so that the first cap member and the second cap member are disengaged from the clamp members by rotating the first cap member and the second cap member about axes of the nozzle and the collection tube, respectively, by an angle of not greater than 180 degrees.

The particle detector may further comprise two packings respectively provided between the first cap member and the first cell body and between the second cap member and the second cell body.

In accordance with further another inventive aspect, there is provided a particle analyzer, which comprises: a particle detector comprising a first electrode and a second electrode for detecting a change in impedance of a liquid containing particles; an electric current supplying circuit for causing an electric current to flow between the first electrode and the second electrode; an amplifier circuit for amplifying a voltage generated between the first electrode and the second electrode and outputting the amplified voltage when the electric current flows between the first electrode and the second electrode; a DC power supply circuit for applying a circuit driving voltage to the electric current supplying circuit and the amplifier circuit via a positive voltage application interconnection and a negative voltage application interconnection; and a conductive case which houses the particle detector; wherein the conductive case comprises an outer conductive case and an inner conductive case insulated from each other, the outer conductive case being grounded, the inner conductive case being electrically connected to the negative voltage application interconnection. According to this inventive aspect, the particle detector is housed in the conductive case having a double structure with the outer case being grounded and with the inner case being connected to the amplifier circuit via the negative voltage application interconnection. Therefore, the particle detector can effectively be shielded from external electromagnetic noises, thereby ensuring a higher level of measurement accuracy.

The conductive case may comprise an openable cover.

The inner conductive case may comprise an electrically conductive bottom plate provided on a metal panel in an insulative manner, and an inner conductive cover of a box shape pivotally supported on the bottom plate and covering the bottom plate in an openable manner, and the outer conductive case may comprise an outer cover of a box shape covering the inner conductive cover with the intervention of an insulative material, wherein the particle detector is disposed on the bottom plate.

The particle analyzer may further comprise an electrically conductive elastic member fixed onto the metal panel, wherein the inner conductive cover is in contact with the bottom plate and the outer conductive cover is in contact with the electrically conductive elastic member when the inner conductive cover covers the bottom plate.

With reference to the attached drawings, the present invention will hereinafter be described in detail by way of embodiments thereof.

Construction of Particle Analyzer

Figure 2:
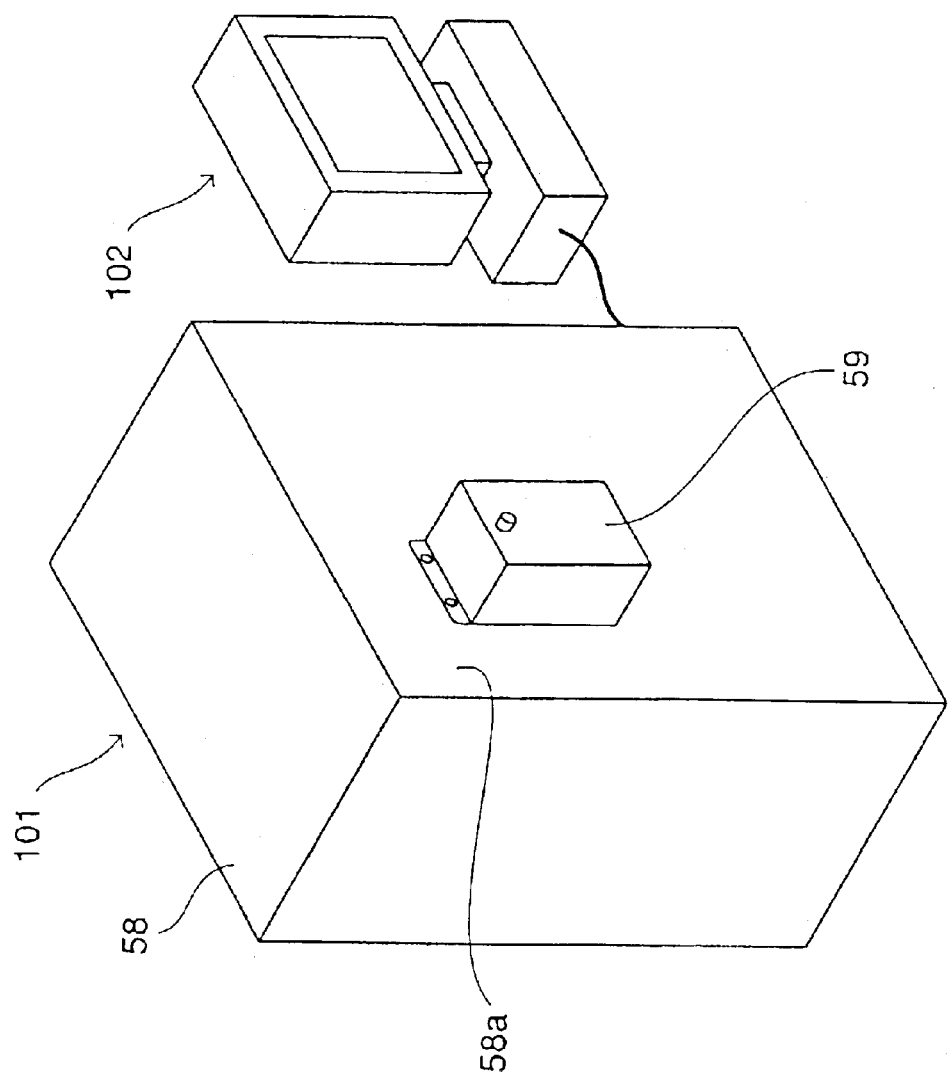
FIG. 2 is a perspective view of the particle analyzer according to the present invention.

FIG. 1 is a block diagram illustrating the construction of a particle analyzer according to the present invention, and FIG. 2 is a perspective view illustrating the appearance of the particle analyzer. The particle analyzer includes a particle analyzer main body 101 and a personal computer 102.

The main body 101 includes a sampling section 51, a dilution/reaction section 52, an electrical resistance type detection section 53, a flow cytometric detection section 54, and a calorimetric detection section 55. The personal computer 102 includes a data processing section 56 and an output section 57.

The sampling section 51 sucks a blood sample as a liquid containing particles to be analyzed from a sample vessel, then meters a predetermined amount of the blood sample, and supplies the metered blood sample into the dilution/reaction section 52. The dilution/reaction section 52 dilutes the metered blood sample at a predetermined dilution factor, then causes the diluted blood sample with a necessary reagent, and supplies the resulting blood sample to the electrical resistance type detection section 53, the flow cytometric detection section 54 and the calorimetric detection section 55.

The electrical resistance type detection section 53 measures the number of red blood cells, the number of platelets and the like in the blood sample by an electrical detection zone method. The flow cytometric detection section 54 measures the number of white blood cells in the blood sample, and obtains data for classification of the white blood cells by a flow cytometric method. The calorimetric detection section 55 measures the concentration of hemoglobin in the blood sample by a colorimetric method.

The data processing section 56 calculates levels of desired measurement items on the basis of measurement data obtained by the respective detection sections 53, 54, 55, and causes the output section 57 to output the calculation results in the form of a numerical list or a scattergram.

The data processing section 56 includes a CPU, a ROM and a RAM, and the output section 57 includes a CRT and a printer. As shown in FIG. 2, the main body 101 includes a metal housing 58, in which the sampling section 51, the dilution/reaction section 52 and the detection sections 53, 54, 55 are housed.

However, a particle detector 1 (see, FIGS. 3–5) of the electrical resistance type detection section 53 is provided on an outer side of a front panel 58a of the housing 58 and covered with an openable metal cover 59 for noise prevention, so that a maintenance operation (check and maintenance operation) can easily be performed on the particle detector 1.

Construction of Particle Detector

Figure 3:
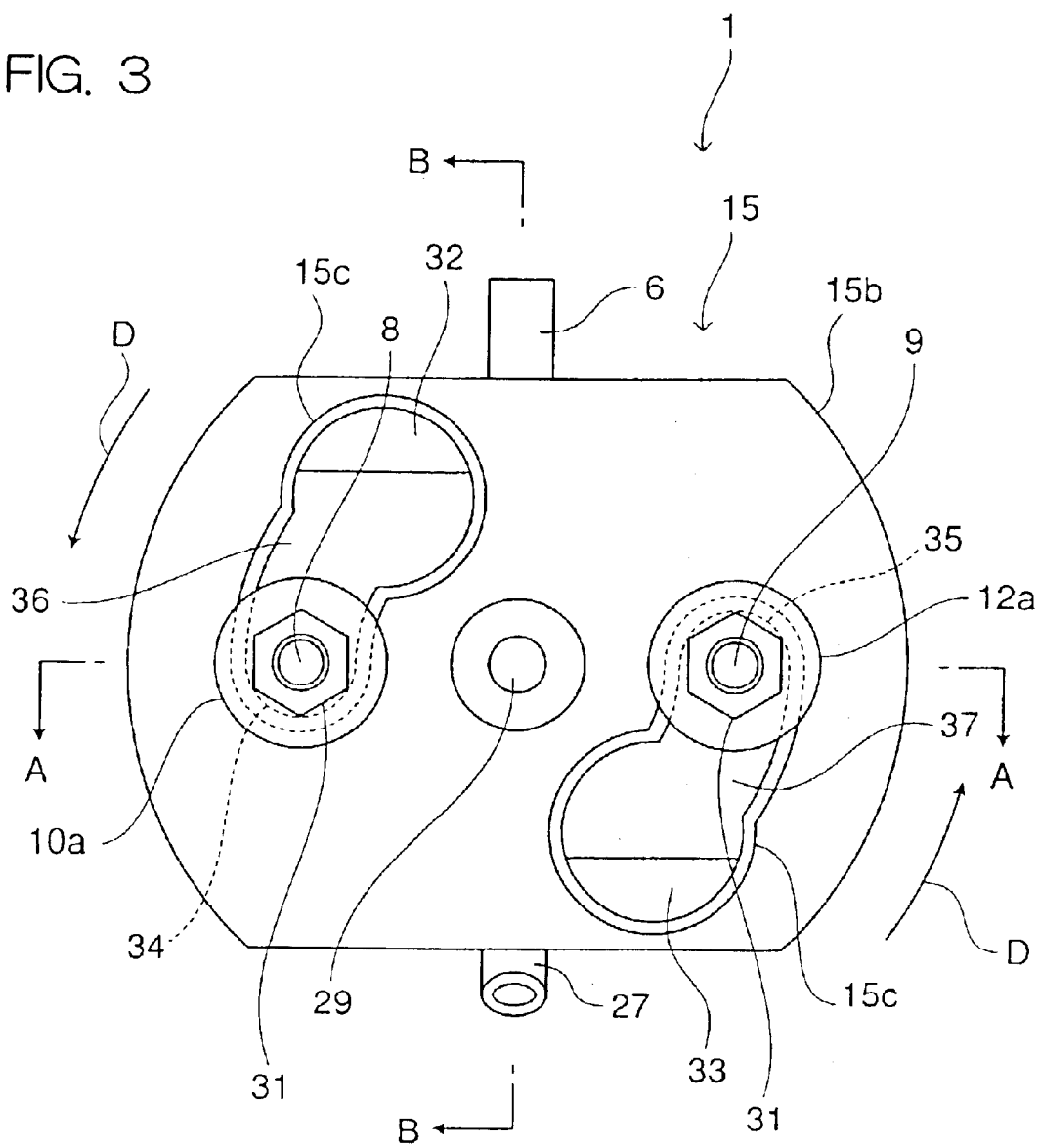
FIG. 3 is a side view of a particle detector according to the present invention.
Figure 4:
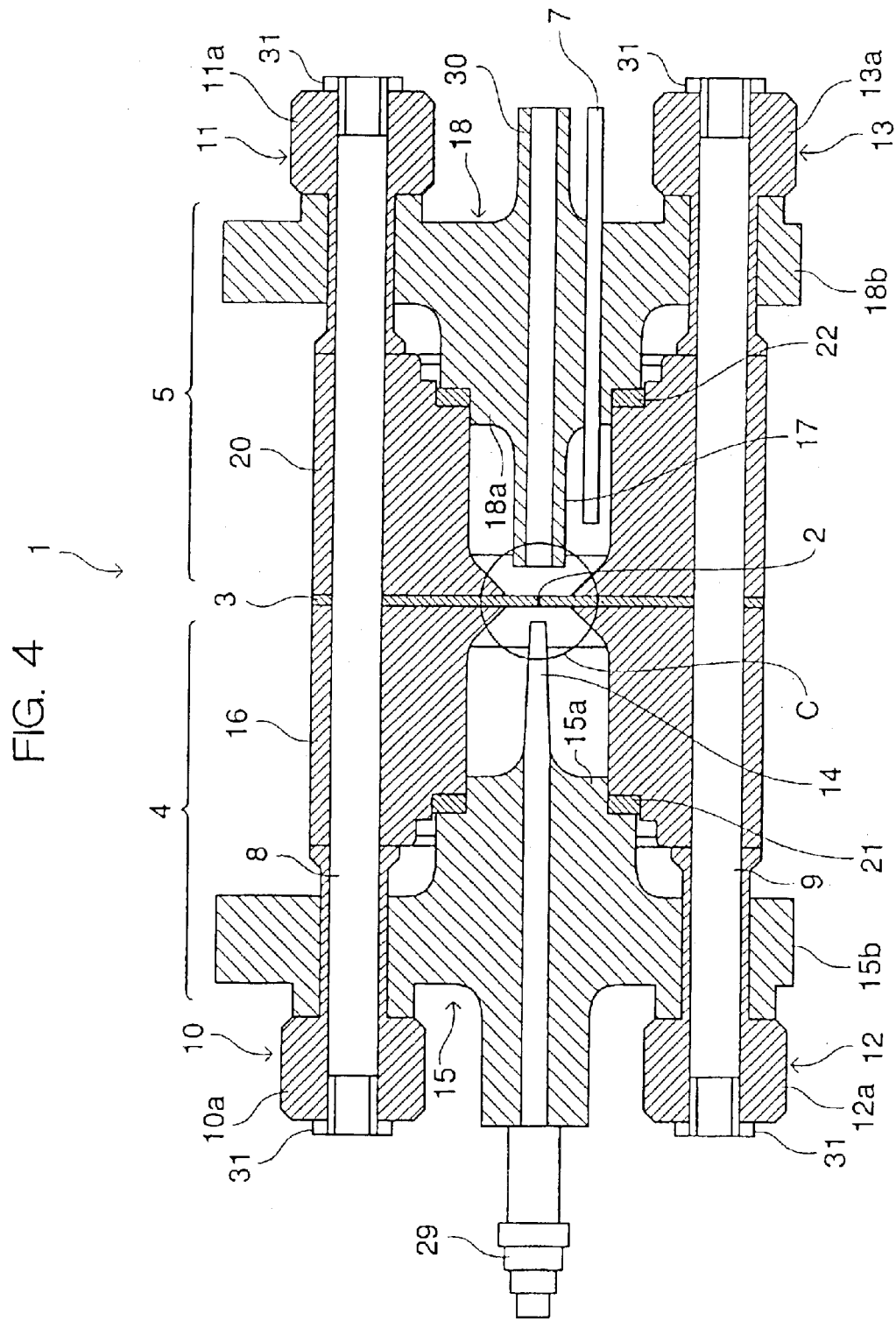
FIG. 4 is a sectional diagram as viewed in an arrow direction A—A in FIG. 3.
Figure 5:
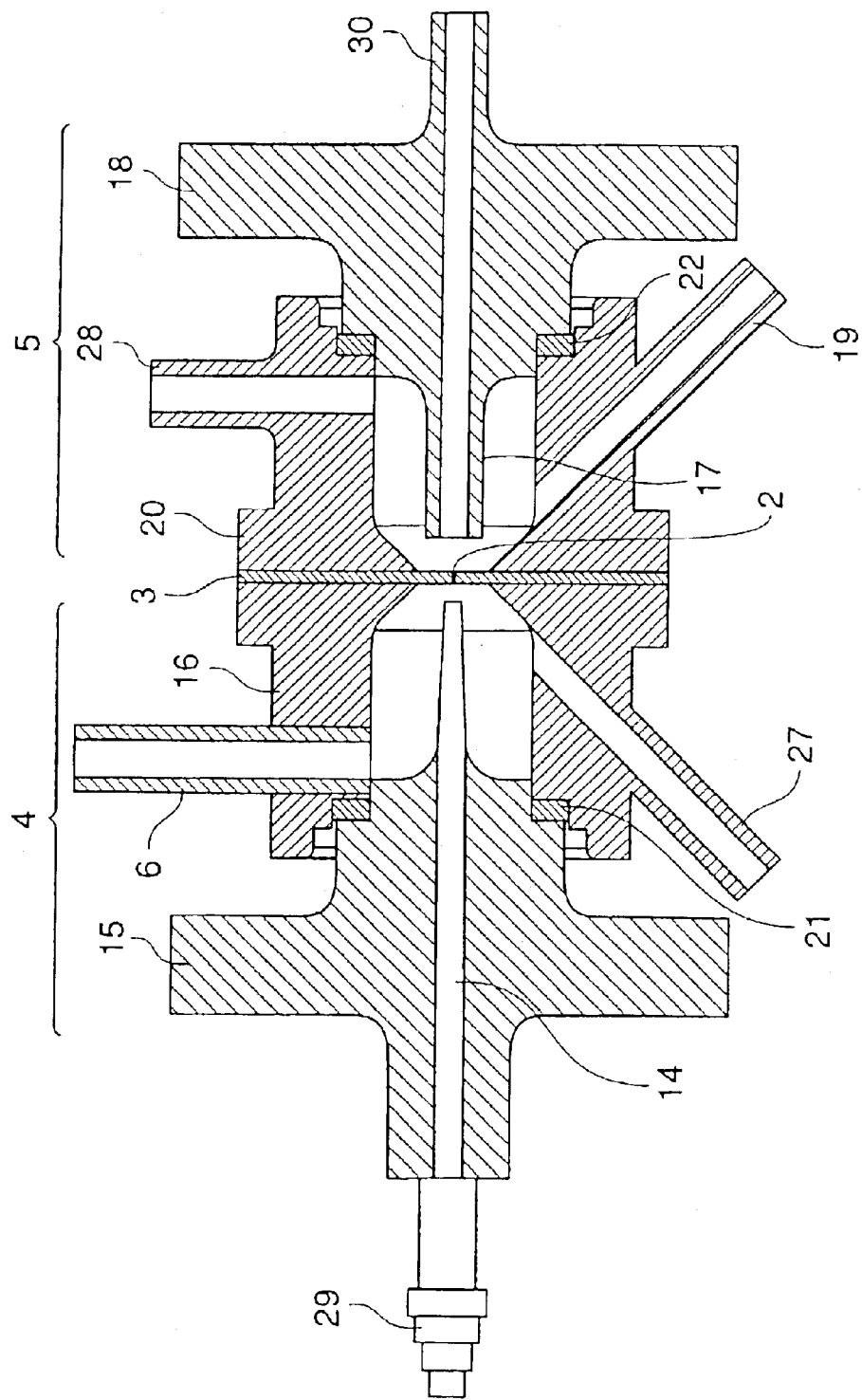
FIG. 5 is a sectional diagram as viewed in an arrow direction B—B in FIG. 3.
Figure 6:
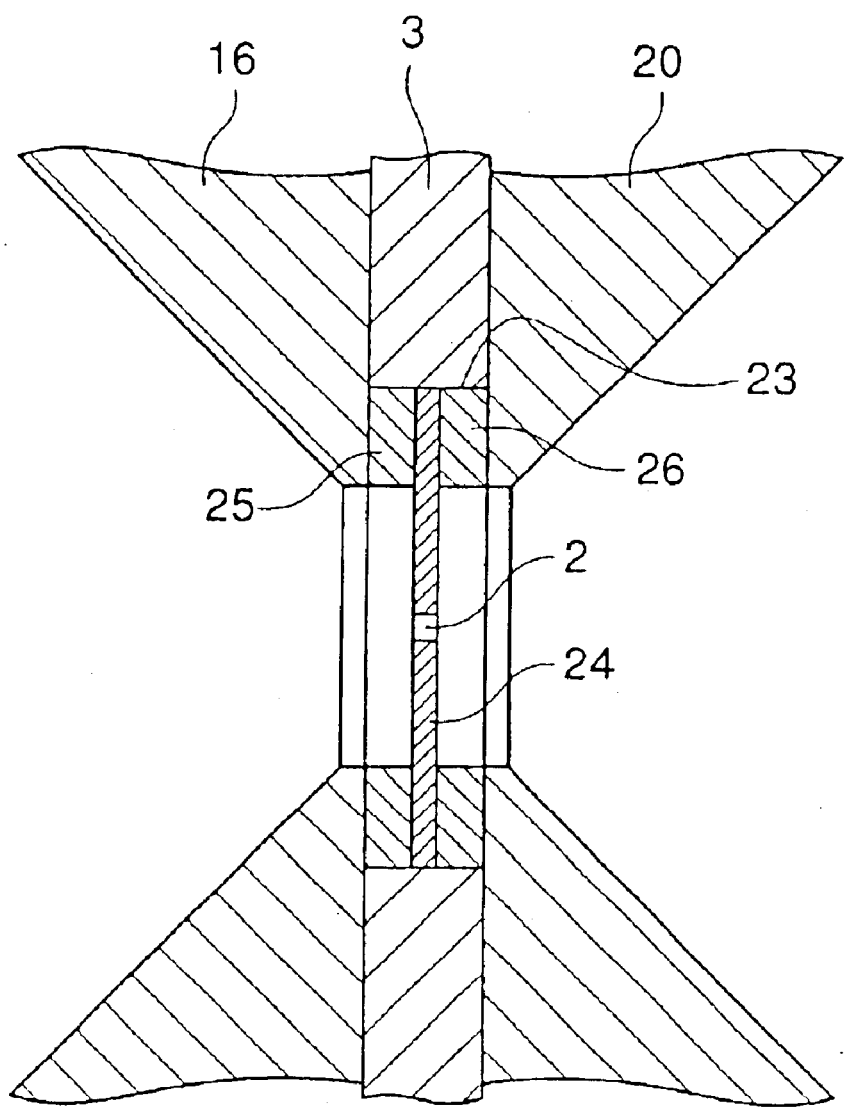
FIG. 6 is an enlarged diagram illustrating a portion C in FIG. 4.

FIG. 3 is a side view of the particle detector 1 housed in the cover 59. FIG. 4 is a sectional diagram as viewed in an arrow direction A—A in FIG. 3, and FIG. 5 is a sectional diagram as viewed in an arrow direction B—B in FIG. 3. FIG. 6 is an enlarged view of a portion C in FIG. 4.

As shown, the particle detector 1 includes a plate member 3, a first cell 4, a second cell 5, and two through-shafts 8, 9. The plate member 3 has a through-hole 2 for particle detection. The first cell 4 includes a first cap member 15 and a cylindrical cell body 16, while the second cell 5 includes a second cap member 18 and a cylindrical second cell body 20. The plate member 3 may be constructed integrally with the first cell body 16 or the second cell body 20.

As shown in FIG. 4, the shafts 8, 9 extend through the first and second cell bodies 16, 20 provided on opposite sides of the plate member 3, and tubular stoppers 10, 11, 12, 13 are fitted around opposite end portions of the shafts 8, 9.

Nuts 31 are threaded with male thread portions provided on opposite ends of the shafts 8, 9, so that the first and second cell bodies 16, 20 are liquid-tightly connected to the plate member 3 by clamping forces of the nuts 31.

The first cap member 15 and the second cap member 18 include a nozzle 14 and a collection tube 17, respectively, which extend therethrough along center axes thereof.

The first cap member 15 includes a projection 15a and a flange member 15b, and the second cap member 18 includes a projection 18a and a flange member 18b.

With the projections 15a, 18a respectively inserted in openings of the first and second cell bodies 16, 20, the flange members 15b and 18b are respectively pressed against the first and second cell bodies 16 and 20 in engagement with annular portions 10a, 12a of the stoppers 10, 12 and the annular portions 11a, 13a of the stoppers 11, 13.

Thus, the first and second cap members 15 and 18 are liquid-tightly connected to the first and second cell bodies 16 and 20 via packings 21 and 22, respectively. At the same time, the first and second cap members 15 and 18 are positioned by the shafts 8, 9 so that the nozzle 14, the through-hole 2 and the collection tube 17 are arranged coaxially with each other.

As shown in FIG. 3, the flange member 15b has insertion holes 32, 33, engagement holes 34, 35, and arcuate connection holes 36, 37 formed therein along arcs around an axis of the nozzle 14. The connection hole 36 connects the insertion hole 32 and the engagement hole 34, and the connection hole 37 connects the insertion hole 33 and the engagement hole 35.

The insertion holes 32, 33 each have an inner diameter greater than the outer diameter of the annular portions 10a, 12a of the stoppers 10, 12. The engagement holes 34, 35 each have an inner diameter smaller than the outer diameter of the annular portions 10a, 12a.

Band-shaped flanges 15c projecting from a surface of the flange member 15b are respectively provided along peripheral edges of the insertion hole 32, the connection hole 36 and the engagement hole 34 and along peripheral edges of the insertion hole 33, the connection hole 37 and the engagement hole 35. Portions of the flanges 15c surrounding the engagement holes 35 have a greater height than the other portions of the flanges 15c.

As shown in FIG. 3, the annular portions 10a, 12a overlie the portions of the flanges 15c surrounding the engagement holes 34, 35. Thus, the first cap member 15 is pressed against the first cell body 16 thereby to be liquid-tightly connected to the first cell body 16 via the packing 21.

The flange member 18b has the same construction as the flange member 15b. Therefore, the second cap member 18 is liquid-tightly connected to the second cell body 20 via the packing 22 in the aforesaid manner.

As shown in FIG. 6, the plate member 3 includes a disk 24 provided in an opening 23 in a center portion thereof and having the through-hole 2, and two ring packings 25, 26 holding the disk 24 therebetween. The first and second cell bodies 16, 20 are liquid-tightly connected to the disk 24 via the packings 25, 26.

As shown in FIG. 5, the first cell body 16 includes a stainless steel nipple 6 inserted therein from an upper side, and a nipple 27 formed integrally therewith and extending downward. The nipple 6 receives and supplies a sheath liquid into the through-hole 2, so that a particle containing liquid injected from the nozzle 14 is enclosed in the sheath liquid to flow through the through-hole 2. A distal tip of the nipple 6 is exposed to the inside of the first cell body 16 so as to serve as an electrode (negative electrode) for measurement.

The nipple 27 receives and sprays a cleaning liquid toward the through-hole 2 obliquely from a lower side. To this end, the nipple 27 has an angle of about 45 degrees with respect to the axis of the nozzle 14.

The second cell body 20 includes nipples 28, 19 formed integrally therewith on its upper and lower sides, respectively. The nipple 19 receives and sprays the cleaning liquid toward the through-hole 2 obliquely from a lower side. To this end, the nipple 19 has an angle of about 45 degrees with respect to the axis of the collection tube 17.

The nipple 28 is provided for discharging the cleaning liquid from the second cell body 20. The second cell body 20 includes a measurement electrode 7 (FIG. 4) exposed therein. The electrode 7 is a platinum electrode rod and serves as a positive electrode. The electrode 7 is fixed to the second cap member 18 parallel to the collection tube 17.

The nozzle 14 includes a tube connector 29 provided at a tail end thereof. Similarly, the collection tube 17 includes a tube connector 30 provided at a tail end thereof.

The nozzle 14 is of stainless steel, and has an inner diameter of 0.2 mm. The disk 24 is of artificial ruby, and has a thickness of 1 mm. The diameter of the through-hole 2 varies depending on the size of a particle to be subjected to the measurement. In the case of red blood cells, the through-hole 2 has a diameter of 50 to 100 $\mu$m.

The first and second cell bodies 16, 20, the first cap member 15 and the second cap member 18 are each produced by injection molding of a thermoplastic polyetherimide which is resistant to chemicals.

The nipple 27 is formed integrally with the first cell body 16, and the nipples 19 and 28 are formed integrally with the second cell body 20. The nozzle 14, the electrode-doubled nipple 6 and the electrode 7 are press-fitted into the first cap member 15, the first cell body 16 and the second cap member 18, respectively, after the injection molding, and fixed by an adhesive.

Disassembly and Assembly of Particle Detector

An explanation will be given to how to disassemble and assemble the particle detector when a maintenance operation is performed for removal of substances deposited in and around the through-hole 2.

Figure 7:
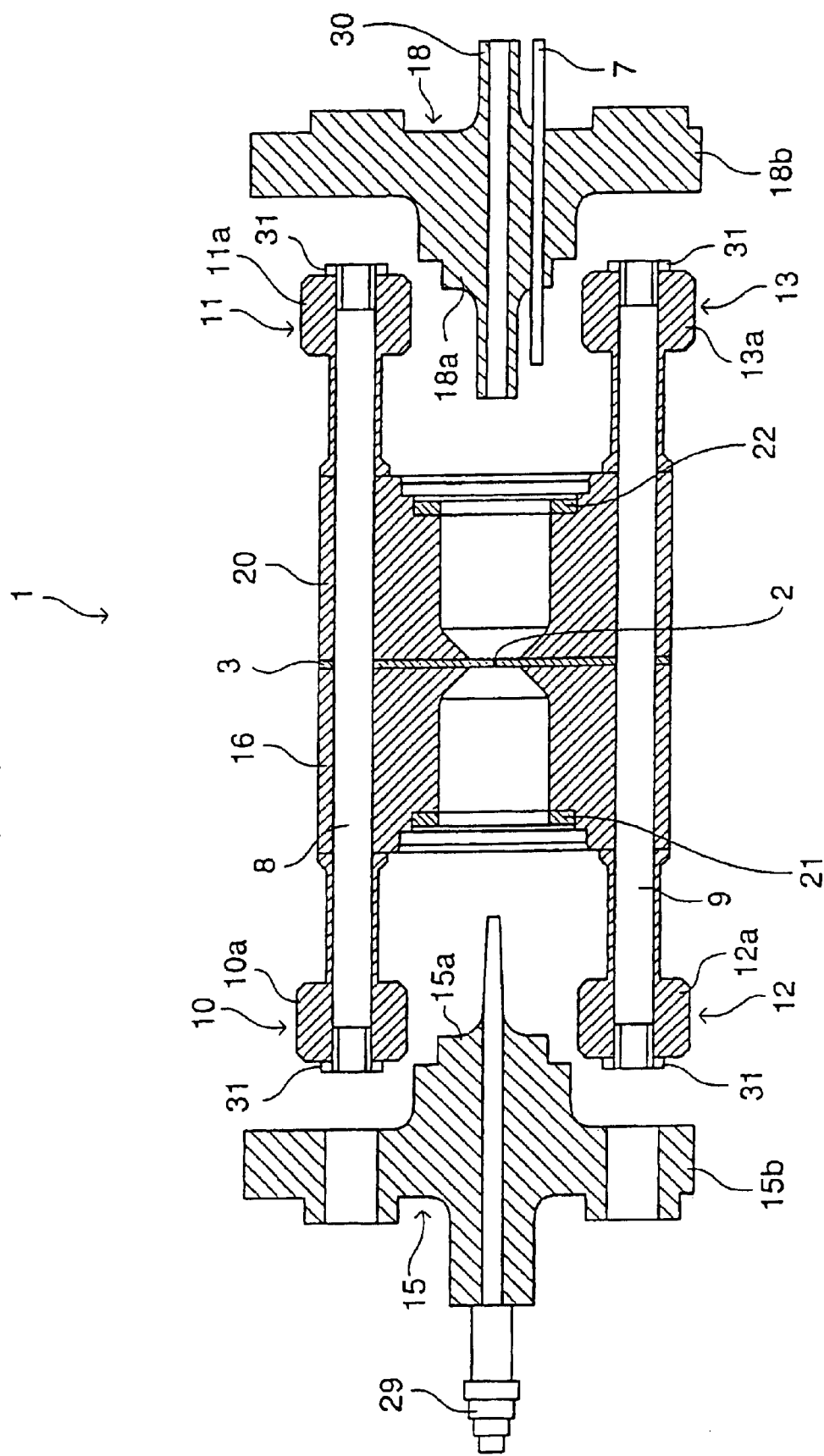
FIG. 7 is an exploded diagram of the particle detector shown in FIG. 4.

An operator first holds the flange member 15b shown in FIG. 3, and then rotates the flange member 15b about 45 degrees in an arrow direction D (counterclockwise). Thus, the annular portions 10a, 12a are relatively moved to the two insertion holes 32, 33 of the flange member 15b. Then, the operator holds the flange member 15b to withdraw the first cap member 15 from the first cell body 16 as shown in FIG. 7.

The second cap member 18 is withdrawn from the second cell body 20 by handling the flange member 18b in the same manner as described above. Then, the operator inserts a thin brush into the through-hole 2 from the openings of the first and second cell bodies 16, 20 to remove the substances deposited in and around the through-hole 2 from the opposite sides of the through-hole 2.

The particle detector 1 is assembled to the original state in reserve order to the disassembling operation. More specifically, the operator holds the flange member 15b of the first cap member 15 to insert the annular members 10a, 12a of the stoppers 10, 12 into the insertion holes 32, 33 of the flange member 15b. At the same time, the projection 15a is inserted into the opening of the first cell body 16.

Then, the operator presses the flange member 15b against the first cell body 16, and then rotates the flange member 15b about 45 degrees in a direction opposite to the arrow direction D in FIG. 3 (clockwise). Thus, the annular members 10a, 12a are relatively moved to the engagement holes 34, 35 onto the higher portions of the flanges 15c.

Thus, the first cap member 15 is pressed against the first cell body 16, and liquid-tightly connected to the first cell body 16 via the packing 21. Similarly, the second cap member 18 is liquid-tightly connected to the second cell body 20. Thus, the assembling operation is completed.

Construction of Cover for Particle Detector

Figure 8:
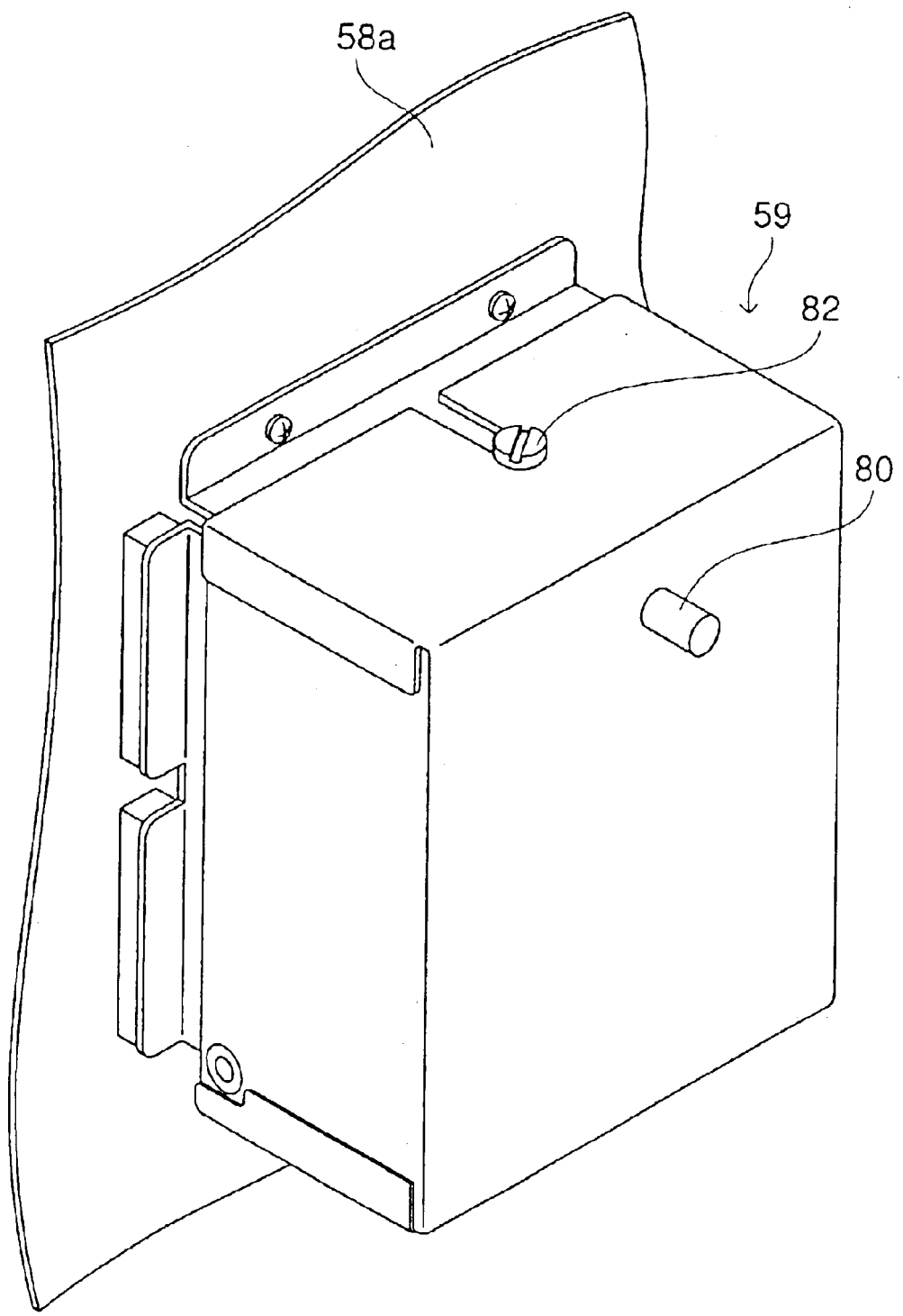
FIG. 8 is a perspective view of a cover for the particle detector according to the present invention.
Figure 9:
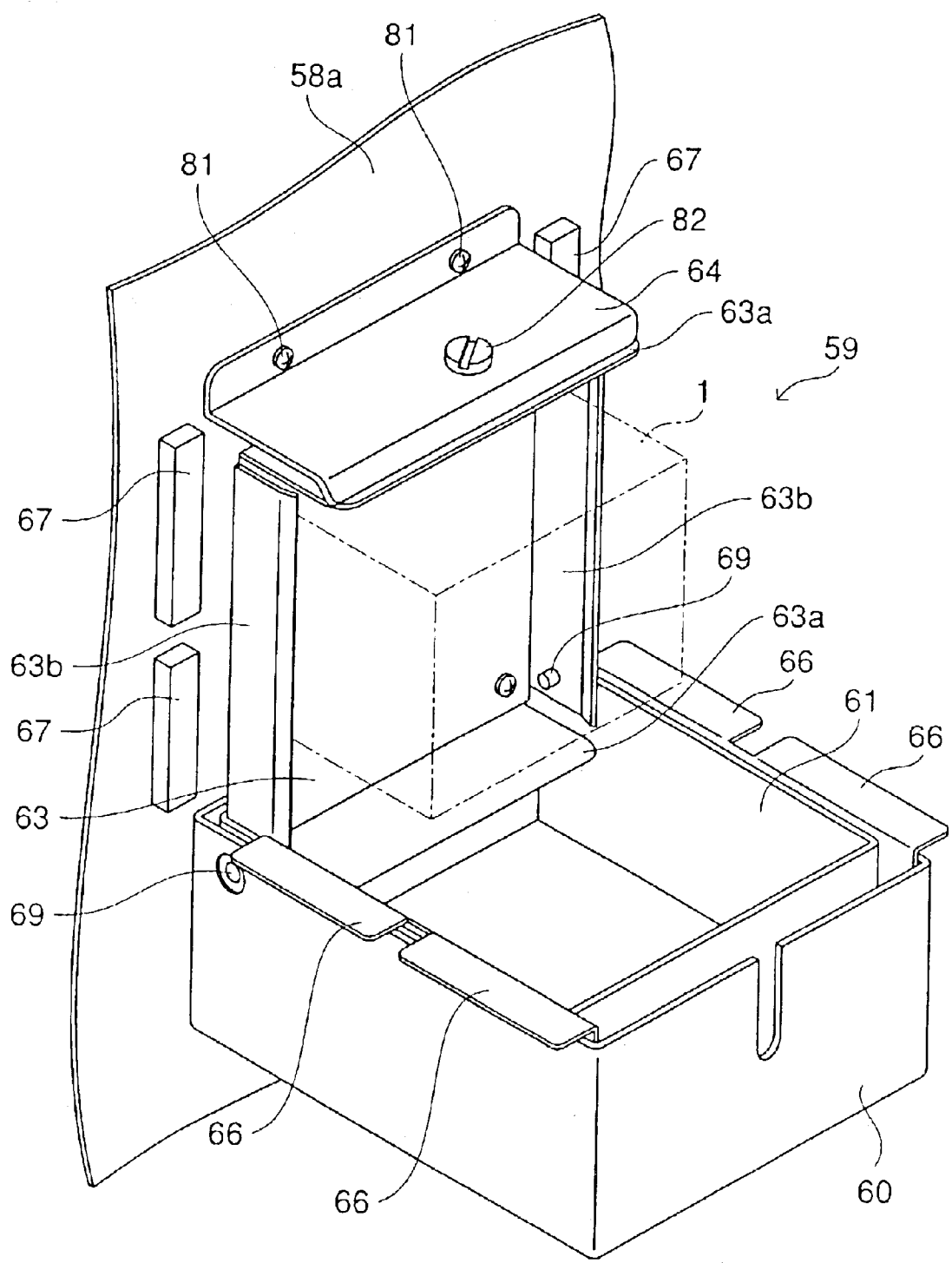
FIG. 9 is a perspective view illustrating a state where the cover shown in FIG. 8 is opened.
Figure 10:
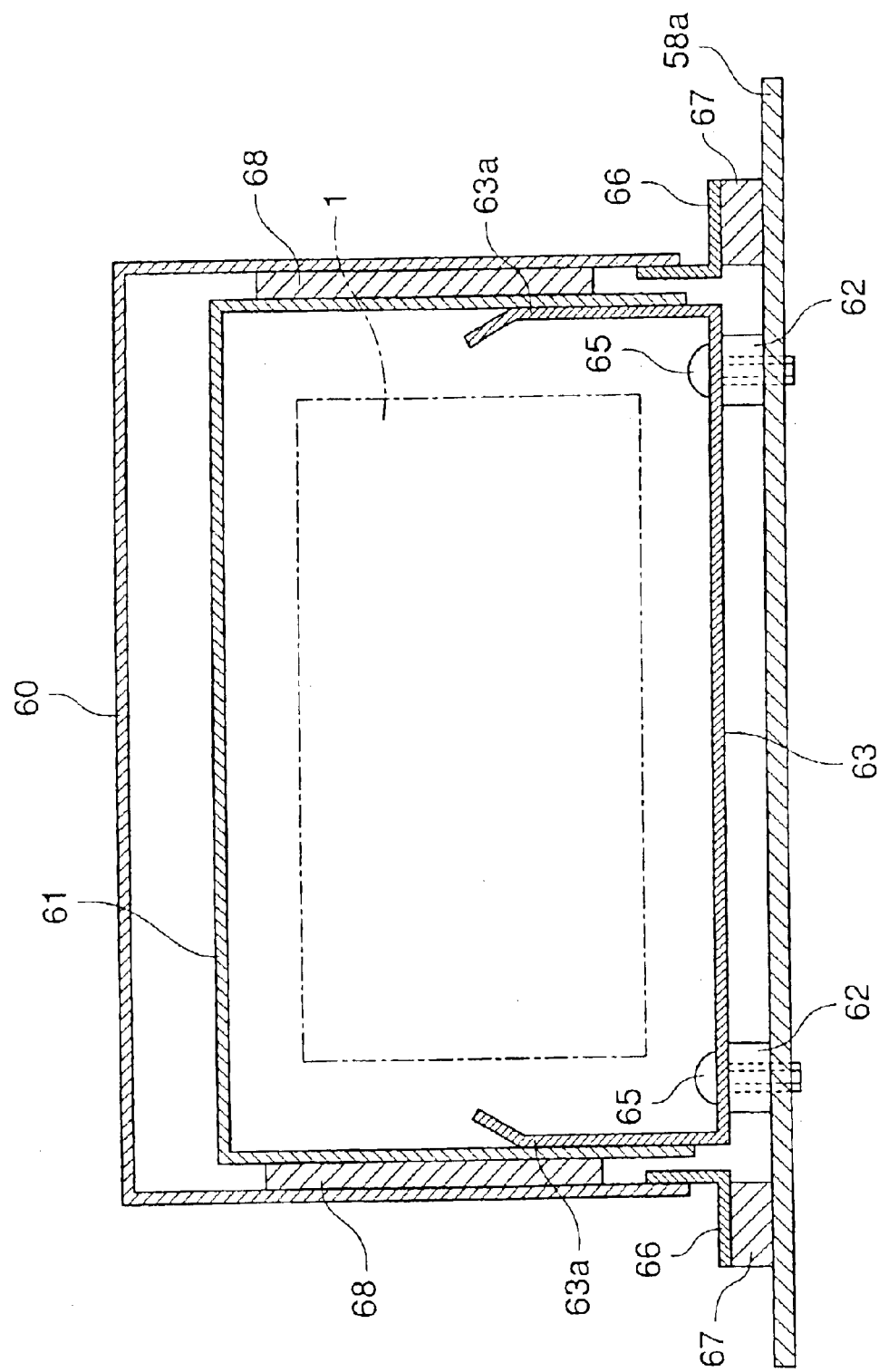
FIG. 10 is a cross sectional view of the cover shown in FIG. 8.

FIG. 8 is a perspective view of the cover 59 for the particle detector 1. FIG. 9 is a perspective view illustrating a state where the cover 59 is opened, and FIG. 10 is a cross sectional view of the cover 59. As shown, the cover 59 is fixed by a screw 82. When the screw 82 is loosened and a knob 80 is pulled forward, the cover 59 is opened so that the particle detector 1 provided therein is exposed.

Since the cover 59 is of a double structure including an outer cover 60 and an inner cover 61. The inner cover 61 includes a bottom plate 63, which is fixed on the front panel 58a via insulative bushes 62 by screws 65 of an insulative resin (see, FIG. 10). The bottom plate 63 includes two transverse auxiliary side plates 63a and two longitudinal auxiliary side plates 63b projecting from the periphery of the bottom plate 63. The auxiliary side plates 63a, 63b are brought into resilient contact with an interior surface of the inner cover 61 when the cover 59 is closed.

A single auxiliary side plate 64 for the outer cover 60 is fixed to the front panel 58a by metal screws 81. When the cover 59 is closed, the auxiliary side plate 64 is brought into resilient contact with an interior surface of the outer cover 60. Then, the outer cover 60 is fixed to the auxiliary side plate 64 by the metal screw 82.

The outer cover 60 includes four contact plates 66 spot-welded to peripheral edges of an opening of the outer cover 60. Correspondingly to the contact plates 66, four electrically conductive elastic members 67 are fixed to the front panel 58a. When the cover 59 is closed, the four contact plates 66 are brought into resilient contact with the corresponding elastic members 67.

As shown in FIG. 10, the outer cover 60 is fixed to the inner cover 61 via insulative members 68. As shown in FIG. 9, the inner cover 61 is supported by the two longitudinal auxiliary side plates 63b pivotally about two support pins 69, whereby the cover 59 can be opened and closed.

The outer cover 60, the inner cover 61, the auxiliary side plates 63a, 63b, 64 and the contact plates 66 are formed from a metal plate (e.g., a stainless steel plate). Therefore, the particle detector 1 is enclosed by two conductive cases insulated from each other when the cover 59 is closed. It is noted that the electrically conductive elastic members 67 can easily be prepared by bonding electrically conductive tapes on sponge rubber pieces.

Figure 11:
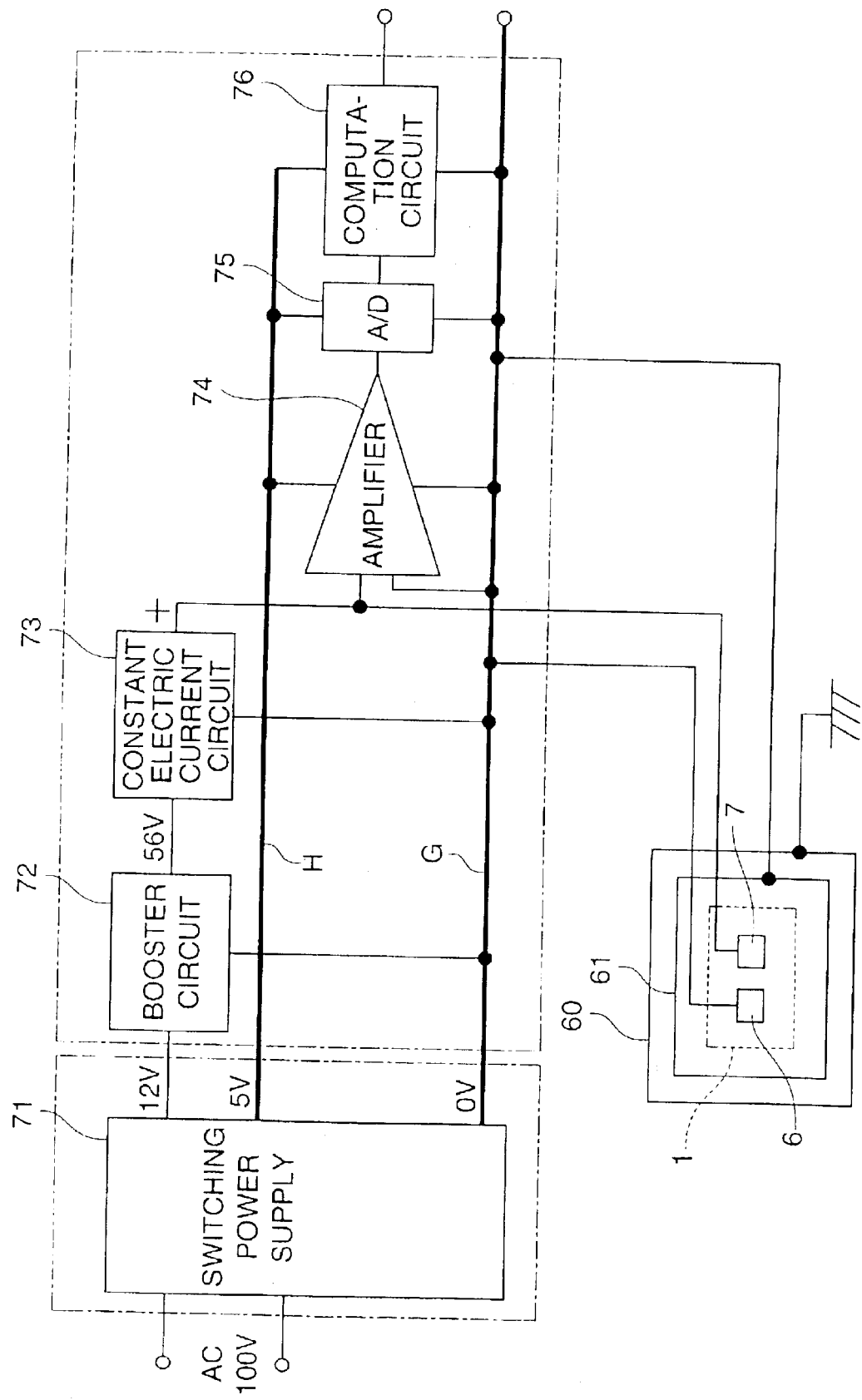
FIG. 11 is an electric circuit diagram of the blood analyzer according to the present invention.

Construction and Operation of Electric Circuit of Electrical Resistance Type Detection Section FIG. 11 is a circuit diagram illustrating an electric circuit of the electrical resistance type detection section 53. When an AC 100V voltage is inputted to a switching power supply circuit 71 from a commercial power supply as shown in FIG. 11, the switching power supply circuit 71 transforms AC 100V into DC 5V and DC 12V, and outputs DC 5V and DC 12V with a ground line G employed as a common negative electrode.

A booster circuit 72 boosts DC 12V to DC 56V, and inputs DC 56V to a constant electric current circuit 73 with its negative electrode connected to the ground line G.

The constant electric current circuit 73 applies DC 56V under no load between the electrode 6 (negative electrode) and the electrode 7 (positive electrode) of the particle detector 1. When the particle containing liquid enclosed in the sheath liquid passes through the through-hole 2 in the particle detector 1 with a constant electric current being supplied between the electrodes 6 and 7 from the constant electric current circuit 73, an electrical resistance (or impedance) between the electrodes 6 and 7 changes, and the change is represented by a variation in voltage (voltage pulse) between the electrodes 6 and 7.

The voltage between the electrodes 6 and 7 is amplified by an amplifier 74, and the amplified voltage is converted into a digital signal by an A/D converter 75. A computation circuit 76 calculates the size and number of particles and like data on the basis of the digital signal, and outputs the calculation results to the personal computer 102 (FIG. 1).

In the circuit shown in FIG. 11, the positive electrode and the negative electrode of the switching power supply circuit 71 are respectively connected to a power supply line H and the ground line G to output the 5V voltage. The amplifier 74, the A/D converter 75 and the computation circuit 76 are connected between the lines H and G, and driven by receiving the voltage from the lines H and G.

Measures against Noises for Particle Detector

As shown in FIGS. 8 to 10, the particle detector 1 is covered with the cover 59 of the double structure including the outer cover 60 and the inner cover 61. As shown in FIG. 11, the outer cover 60 is grounded via the front panel 58a of the housing 58, and the inner cover 61 is connected to the ground line G of the electric circuit. With this arrangement, the particle detector 1 is shielded from external noises, so that requirements of the EMC regulations related to the electromagnetic waves can be satisfied.

Even if the particle detector 1 covered with the cover 59 is subjected to external radio waves with a field intensity of 3 V/m and a frequency of 1 kHz resulting from AM modulation of 80 MHz to 1 GHz radio waves, it is confirmed that the output of the amplifier 74 is not influenced by the radio waves.

Removal of Air Bubbles in Particle Detector

When the particle containing liquid flows together with the sheath liquid from the first cell 4 to the second cell 5 through the through-hole 2 for the particle detection in the particle detector 1, air bubbles are liable to occur in and around the through-hole 2. Where the amount of the air bubbles increases, the air bubbles disturb the detection voltage between the electrodes 6 and 7, so that information on the particles is erroneously detected.

Therefore, the cleaning liquid is sprayed into and around the through-hole 2 from the nipples 19, 27 shown in FIG. 5 immediately before the measurement is performed on every sample, whereby air bubbles adhering or floating in and around the through-hole 2 are removed and discharged together with the cleaning liquid from the nipples 28, 6. Thus, the particle detector 1 ensures a higher level of detection accuracy.

Figure 12:
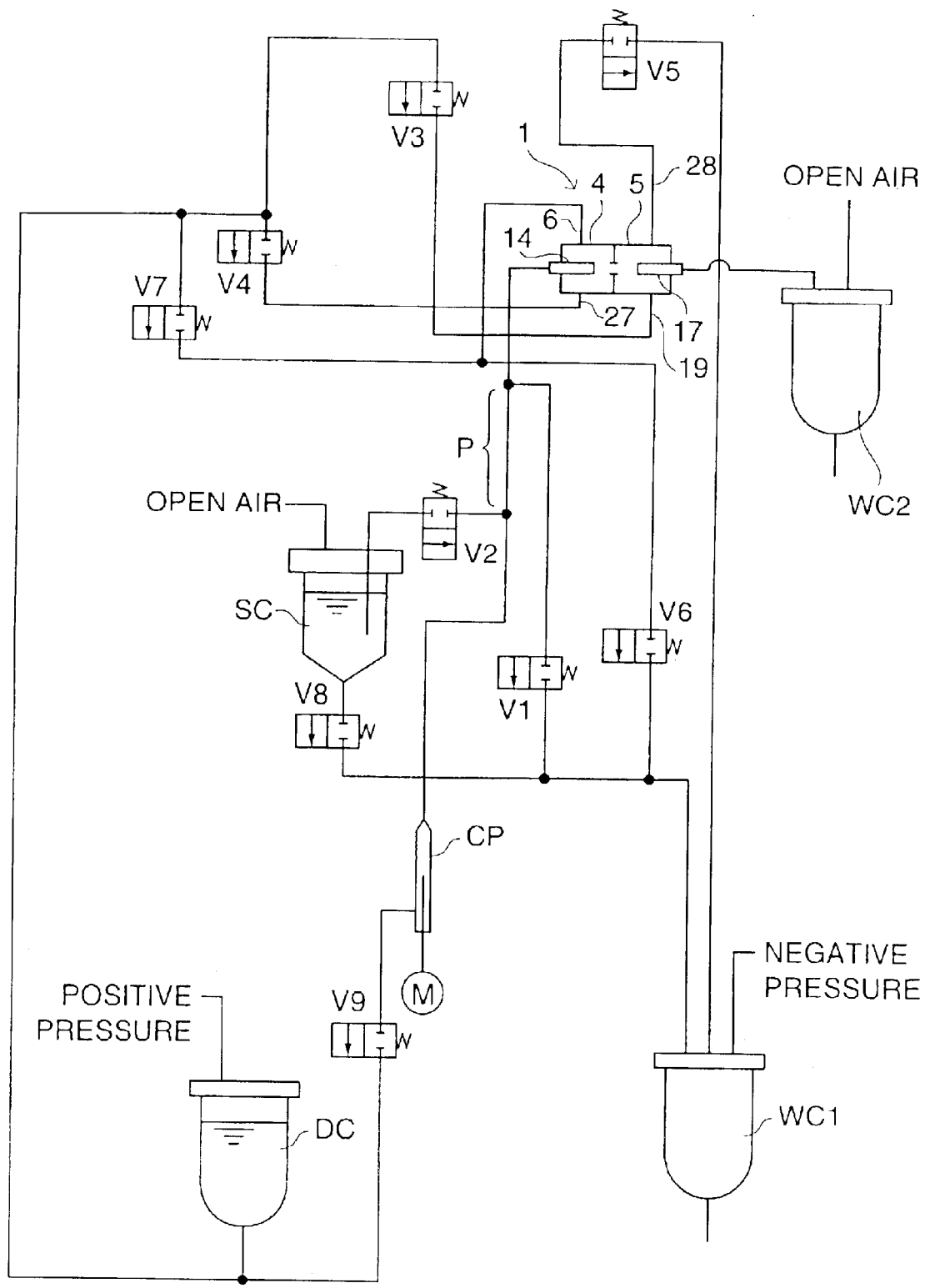
FIG. 12 is a fluid circuit diagram of the particle analyzer according to the present invention.

Construction and Operation of Fluid Circuit of Electrical Resistance Type Detection Section FIG. 12 is a flow circuit diagram of the electrical resistance type detection section 53 employing the particle detector 1. As shown, valves V1, V2 are opened, whereby a red blood cell measurement sample is sucked into a flow path P from a sample chamber SC by a negative pressure of a drainage chamber WC1 and retained in the flow path P. It is noted that the red blood cell measurement sample is prepared by diluting the blood sample in the dilution/reaction section 52 (FIG. 1) and preliminarily stored in the sample chamber SC.

The valves V1, V2 are closed and valves V3, V4, V5, V6 are opened, whereby a diluent is supplied as the cleaning liquid into the nipples 27, 19 from a diluent chamber DC by a positive pressure. Then, the diluent is sprayed in and around the through-hole 2 for cleaning the first and second cells 4, 5 and removing air bubbles, and discharged through the nipples 6, 28 into the drainage chamber WC1.

The valves V3, V4, V5, V6 are closed and a valve V7 is opened, whereby the diluent is supplied as the sheath liquid into the nipple 6 from the diluent chamber DC by a positive pressure and discharged into a drainage chamber WC2 through the through-hole 2 and the collection tube 17. Thus, a sheath liquid flow passing through the through-hole 2 is formed.

A syringe pump CP is operated for discharge in this state, whereby the sample retained in the flow path P is pushed out to be injected into the through-hole 2 from the nozzle 14. The injected sample, which is enclosed in the sheath liquid, passes through the through-hole 2, and is discharged into the drainage chamber WC2 through the collection tube 17.

When the sample is enclosed in the sheath liquid to pass through the through-hole 2, the change in impedance between the electrode 6 (FIG. 3) and the electrode 7 (FIG. 2) is measured by the measurement circuit shown in FIG. 11. Upon completion of the measurement, the syringe pump CP is stopped. Then, a valve V8 is opened, whereby the residue of the sample in the sample chamber SC is discharged into the drain chamber WC1.

Then, the valves V2, V9 are opened (with the valve V8 kept open), whereby the diluent is supplied as the cleaning liquid into the syringe pump CP, a sample suction flow path and the sample chamber SC from the diluent chamber DC.

After a lapse of a predetermined period, the valves V2, V8 are closed (with the valve V9 kept open) and the valve V1 is opened, whereby the diluent is supplied as the cleaning liquid into the syringe pump CP and the flow path P from the diluent chamber DC.

After a lapse of a predetermined period, the valve V1 is closed (with the valve V9 kept open), the diluent is supplied as the cleaning liquid into the syringe pump CP, the flow path P and the nozzle 14. After a lapse of a predetermined period, the valve V9 is closed to complete the cleaning.

What is claimed is:

1. A particle detector comprising:
   first and second cells, the first cell supplying a liquid containing particles to the second cell;
   electrodes respectively provided in the first cell and the second cell;
   a plurality of shafts; and
   clamp members engaged with the respective shafts;
   the first cell and the second cell being arranged in alignment with each other; the shafts extending through the first cell and the second cell along the alignment of the first cell and the second cell; the clamp members clamping the first cell and the second cell along the alignment.

2. A particle detector as set forth in claim 1, wherein a plate member formed with a through-hole is interposed between the first cell and the second cell.

3. A particle detector as set forth in claim 2, wherein the plate member comprises a flat piece formed with the through-hole.

4. A particle detector as set forth in claim 1, wherein the first cell comprises a flat piece formed with a through-hole.

5. A particle detector as set forth in claim 1, wherein the second cell comprises a flat piece formed with a through-hole.

6. A particle detector as set forth in claim 1, wherein a flat piece formed with a through-hole is interposed between the first cell and the second cell.

7. A particle detector as set forth in claim 1, wherein the first cell comprises a nozzle which discharges the liquid containing particles, and the second cell comprises a collection tube which collects the liquid containing particles discharged from the nozzle, wherein the first cell and the second cell are connected to each other so that the nozzle and the collection tube are arranged coaxially with each other.

8. A particle detector as set forth in claim 7, wherein the first cell comprises a nipple which receives a sheath liquid to be supplied to the second cell, and the collection tube further collects the supplied sheath liquid.

9. A particle detector as set forth in claim 1, wherein the first cell comprises a nozzle support having a nozzle which discharges the liquid containing particles, and a first cell body having a nipple which receives a sheath liquid to the first cell.

10. A particle detector as set forth in claim 9, wherein the nozzle support and the first cell body are liquid-tightly connected to each other via a packing.

11. A particle detector as set forth in claim 1, wherein the second cell comprises a collection tube support having a collection tube which collects the liquid containing particles supplied from the first cell, and a second cell body having a nipple which receives a cleaning liquid to the second cell.

12. A particle detector as set forth in claim 11, wherein the collection tube support and the second cell body are liquid-tightly connected to each other via a packing.

13. A particle analyzer employing a particle detector as set forth in claim 1.

14. A particle detector comprising:
   first and second cells, the first cell supplying a liquid containing particles to the second cell;
   a flat piece formed with a through-hole; and
   electrodes respectively provided in the first cell and the second cell;
   the first cell and the second cell communicating with each other through the through-hole, at least one of the first cell and the second cell comprises a first nipple which receives a cleaning liquid to be sprayed toward the through-hole, and a second nipple which drains the sprayed cleaning liquid.

15. A particle detector as set forth in claim 14, wherein the first cell and the second cell each comprise the first nipple and the second nipple.

16. A particle detector as set forth in claim 14, wherein the first nipple is disposed so that the cleaning liquid is sprayed at an incident angle of 30 to 60 degrees with respect to an axis of the through-hole.

17. A particle detector comprising:
   a first cell that comprises a cylindrical first cell body having openings of its both ends and a first cap member nozzle which discharges a liquid containing particles;
   a second cell a cylindrical second cell body having openings of its both ends and a second cap member having a collection tube which collects the liquid having discharged from the nozzle;
   electrodes respectively provided in the first cell and the second cell; and
   a plurality of shafts extending through the first cap member, the first cell body, the second cell body and the second cap member;
   wherein one opening of the first cell body communicates with one opening of the second cell body through a through-hole, the first cap member liquid-tightly closes the other opening of the first cell body in a removable manner, the second cap member liquid-tightly closes the other opening of the second cell body in a removable manner, the nozzle and the collection tube are arranged coaxially with each other, and the first cap member and the second cap member are removable from the plurality of the shafts.

18. A particle detector as set forth in claim 17, further comprising stoppers provided on opposite ends of the respective shafts, wherein the first cap member and the second cap member are disengageably engaged with the stoppers to close the first cell body and the second cell body, respectively.

19. A particle detector as set forth in claim 18, wherein the first cap member and the second cap member respectively have holes through which the stopper are respectively inserted, wherein the holes are configured so that the first cap member and the second cap member are disengaged from the stoppers by rotating the first cap member and the second cap member about axes of the nozzle and the collection tube, respectively, by an angle of not greater than 180 degrees.

20. A particle detector as set forth in claim 17, wherein at least one of the electrodes is incorporated in the first cap member or the second cap member.

21. A particle detector as set forth in claim 17, further comprising two packings respectively provided between the first cap member and the first cell body and between the second cap member and the second cell body.

22. A particle as set forth in claim 17, wherein the electrodes are respectively provided in the first cell body and the second cell body.

* * * * *